United States Patent
Schafer Elejalde et al.

(10) Patent No.: US 10,265,264 B2
(45) Date of Patent: Apr. 23, 2019

(54) **PROCESSES AND COMPOSITIONS OBTAINED FROM THE *SOLANUM* GENUS OF PLANTS**

(71) Applicant: BIOPROCOL, BIOPROCESOS DE COLOMBIA SAS, Enigado-Antioquia (CO)

(72) Inventors: German Alfredo Schafer Elejalde, Lafayette, IN (US); Guillermo Leon Palacio Gonzalez, Medellin (CO); Carlos Esteban Aristizabal Alzate, Medellin (CO)

(73) Assignee: BIOPROCOL, BIOPROCESOS DE COLOMBIA SAS, Medellin (CO)

( * ) Notice: Subject to any disclaimer, the term of this patent is extended or adjusted under 35 U.S.C. 154(b) by 0 days.

(21) Appl. No.: 15/532,152

(22) PCT Filed: Dec. 1, 2015

(86) PCT No.: PCT/US2015/063197
§ 371 (c)(1),
(2) Date: Jun. 1, 2017

(87) PCT Pub. No.: WO2016/089876
PCT Pub. Date: Jun. 9, 2016

(65) Prior Publication Data
US 2017/0348222 A1  Dec. 7, 2017

(30) Foreign Application Priority Data
Dec. 2, 2014 (CO) .................................. 14-265.330

(51) Int. Cl.
| | | |
|---|---|---|
| A61K 36/00 | (2006.01) | |
| A61K 8/9789 | (2017.01) | |
| A61K 31/706 | (2006.01) | |
| A61Q 19/00 | (2006.01) | |
| A61K 8/63 | (2006.01) | |
| A01N 65/38 | (2009.01) | |
| C07J 71/00 | (2006.01) | |
| A61K 36/81 | (2006.01) | |
| A61K 8/97 | (2017.01) | |
| A01N 43/90 | (2006.01) | |
| A61K 8/31 | (2006.01) | |
| A61K 8/368 | (2006.01) | |
| A61K 8/40 | (2006.01) | |
| A61K 8/41 | (2006.01) | |
| A61K 8/67 | (2006.01) | |
| A61K 8/81 | (2006.01) | |
| A61K 8/86 | (2006.01) | |

(52) U.S. Cl.
CPC ............ *A61K 8/9789* (2017.08); *A01N 43/90* (2013.01); *A01N 65/38* (2013.01); *A61K 8/31* (2013.01); *A61K 8/368* (2013.01); *A61K 8/40* (2013.01); *A61K 8/41* (2013.01); *A61K 8/63* (2013.01); *A61K 8/678* (2013.01); *A61K 8/8152* (2013.01); *A61K 8/86* (2013.01); *A61K 8/97* (2013.01); *A61K 31/706* (2013.01); *A61K 36/81* (2013.01); *A61Q 19/00* (2013.01); *C07J 71/0005* (2013.01); *C07J 71/0052* (2013.01); *A61K 2236/00* (2013.01); *A61K 2800/10* (2013.01); *A61K 2800/30* (2013.01); *Y02A 50/331* (2018.01); *Y02A 50/409* (2018.01); *Y02A 50/423* (2018.01)

(58) Field of Classification Search
CPC ........................................................ A61K 36/00
See application file for complete search history.

(56) References Cited

U.S. PATENT DOCUMENTS

| | | | |
|---|---|---|---|
| 3,960,839 A | 6/1976 | Guerrero | |
| 7,078,063 B2 | 7/2006 | Kuo | |
| 7,479,290 B2 | 1/2009 | Lawson | |
| 8,614,196 B2 * | 12/2013 | Kuo | ......................... A61K 8/97 |
| | | | 514/26 |
| 2004/0030109 A1 | 2/2004 | Carter et al. | |
| 2004/0220115 A1 | 11/2004 | Cham | |
| 2014/0147523 A1 | 5/2014 | Mahmood et al. | |

FOREIGN PATENT DOCUMENTS

| | | |
|---|---|---|
| EP | 0020029 A1 | 12/1980 |
| EP | 2522357 A1 | 11/2012 |

OTHER PUBLICATIONS

Alzerreca et al., "Molluscicidal Steroid Glycoalkaloids Possessing Stereoisomeric Spirosolane Structures," Toxicology Letters, vol. 12, pp. 151-155 (1982).
International Search Report prepared for International Application No. WO/US2015/063197, dated Feb. 5, 2016.
Written Opinion of the International Searching Authority prepared for International Application No. WO/US2015/063197, dated Feb. 5, 2016.
Database GNPD (online) Mintel; "Foot Care Cream," XP055525789, retrieved from www.gnpd.com, Database accession No. 1544249 (May 24, 2011).
Database GNPD (online) Mintel; "Balancing Facial Toner," XP055525792, retrieved from gnpd.com, Database accession No. 1933581 (Nov 26, 2012).

* cited by examiner

*Primary Examiner* — Qiuwen Mi
(74) *Attorney, Agent, or Firm* — Sonapat LLC

(57) ABSTRACT

Pure saponins and processes for making such saponins are described herein. In addition, cosmetic compositions, such as skin care compositions, comprising such saponins and methods for improving skin health and appearance with such skincare compositions are also described herein.

11 Claims, 16 Drawing Sheets

PROCESSES AND COMPOSITIONS OBTAINED FROM THE *SOLANUM* GENUS OF PLANTS

CROSS REFERENCE TO OTHER APPLICATIONS

This international application claims priority to Colombian Patent Application No. 14-265.330 filed on Dec. 2, 2014, the entire disclosure of which is hereby incorporated by reference.

TECHNICAL FIELD

The present invention relates to processes to obtain saponins and sapogenin-rich extract from *Solanum* genus plant fruits as solids and compositions thereof. The solid phase of saponins may be used, for example, in the pharmaceutical, cosmetic, nutraceutical, agricultural and veterinary industries.

BACKGROUND

There is a need in seeking new compounds from natural sources to satisfy the demand for pharmaceutical, cosmetic, nutraceutical, agricultural and veterinary products, which has turned researchers and industries worldwide to develop bioprospecting, which is the study and sustainable use of plant, microorganism and animals biodiversity. In plants and vegetables, bioactive compounds are usually found in very low quantities, making extraction expensive and wasteful. It would be beneficial to have processes for extracting such bioactive compounds in high purity in ways that have minimal impact to the environment while at the same time increasing the yields of such compounds so to be commercially viable.

Saponins are natural glycosides that are widely distributed in the plant kingdom, given they have been detected in more than 500 genera of plants, including the *Solanum* genus. These compounds are attributed with phytoprotection functions in plants because of their fungicidal, antibiotic, insecticidal and molluscicidal properties.

Glycosides from the saponins possess an aglycone skeleton, which can be classified into three groups: steroidal, triterpene and glycoalkaloids. Solasodine glycosides are found in the glycoalkaloids group. Among the saponins that can be found in plants of the *Solanum* genus and which are monoglycosides and diglycosides of solasodine include saponins such as Solasonine (I), Solamargine (II), Solanine (III), Chaconine (IV) Tomatine (V) and Sycophantine (VI) whose structures are set forth below:

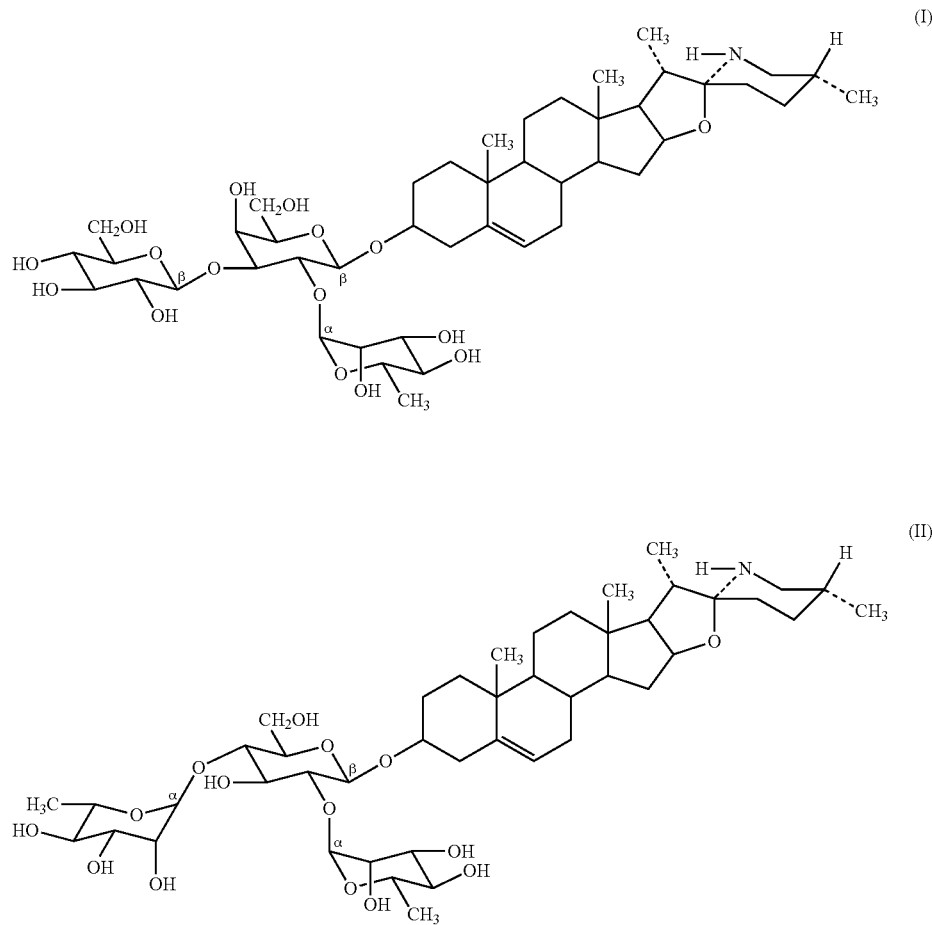

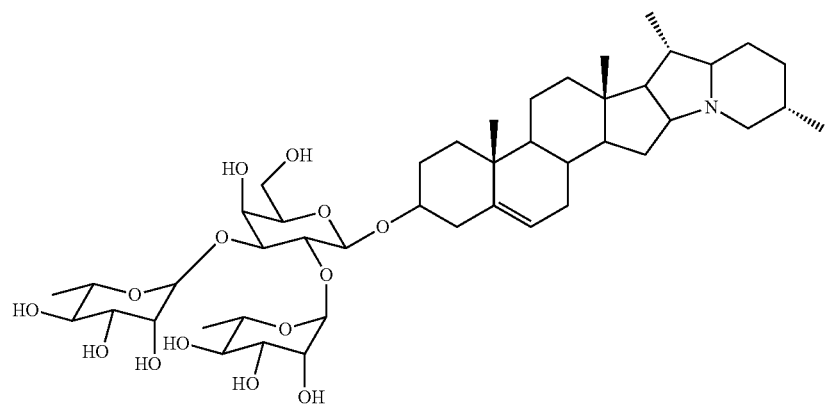
(III)
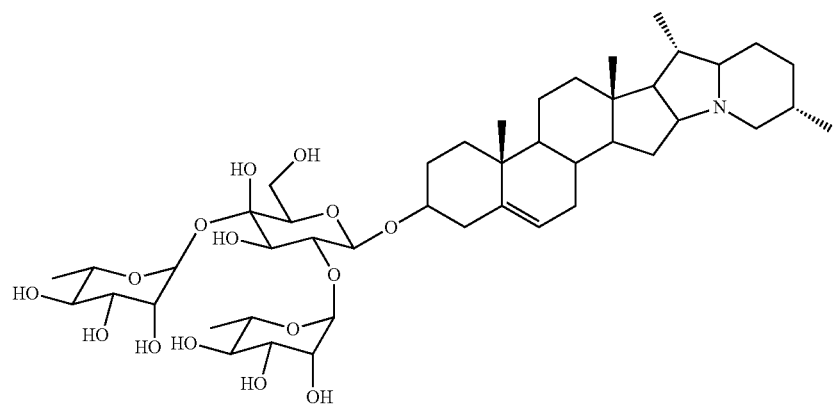
(IV)
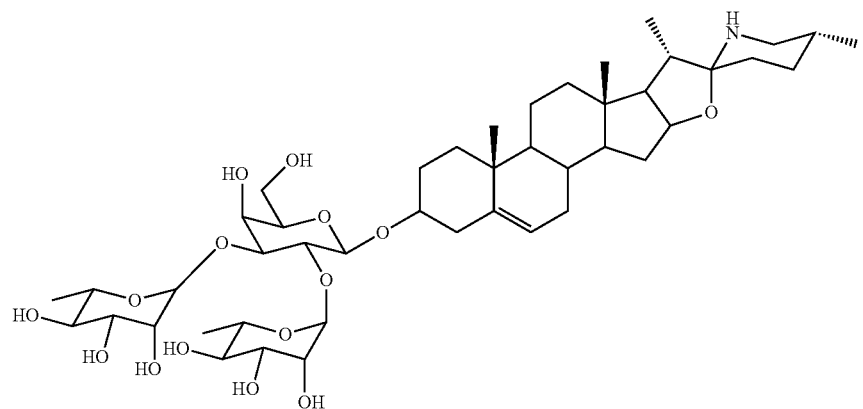
(V)

-continued

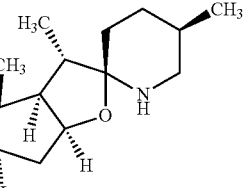
(VI)

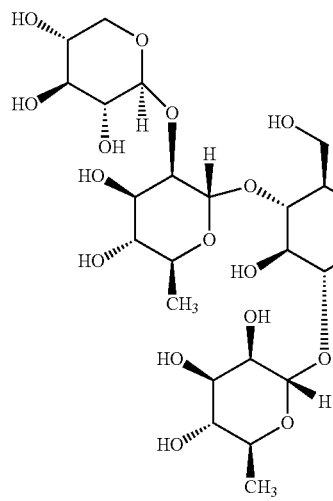

Saponins present in the plants of the *Solanum* genus are also useful as intermediates in the synthesis of contraceptive agents, corticosteroids, sex hormones and have also been proven effective in the treatment of various cancers in humans, showing high selectivity for tumor cells. Further, as antibiotics, these glycosides can inhibit the growth of Gram positive bacteria and have antiparasitic activity against microorganisms, such as *Leishmania amazonenzis* and several species of *Schistosoma* genus which cause leishmaniasis and schistosomiasis.

It has also been found that certain plant extracts of *Solanum* genus rich in saponins, have anti-inflammatory, hypotensive, hypoallergenic, antihistamine and antimicotic activity against fungi and yeast that cause dermatiphytosis and can be employed to improve skin health such as for the treatment of skin ulcerations caused by *L. braziliensis*. Other known uses include treatment of diabetes and high cholesterol.

It has further been found that the hydroalcoholic extracts of plants of the *Solanum* genus, exhibit molluscicidal activity against *Bulinus camerunensis*, and *B. truncates* and *L. cubensis*. Such mollusks are known to damage crops and transmit diseases.

Several processes have been described for obtaining saponins from plants of the *Solanum* genus, such as *S. sodomaem*, *S. incanum*, *S. nigrum* and *S. robustum*. Such processes are typically based on crushed or ground dry fruits, and extractions are performed using various solvents and purification steps. Thus for example, in U.S. Pat. Nos. 3,960,839 and 7,479,290, processes are mentioned wherein a first extraction takes place by mixing the crushed and milled dry fruits with methanol/water solutions, using a Soxhlet apparatus.

In such disclosed processes, a second extraction stage is employed using a pH 3-5 acetic acid or formic acid solutions, in which the residual plant material from the first extraction or the dry hydroalcoholic extract obtained was immersed, as mentioned in U.S. Pat. No. 7,479,290.

In other processes, the addition of strong bases (alkali, ammonium) to solutions resulting from the hydroalcoholic and acid extraction are performed in order to precipitate the crude Solasodine glycosides. Thus, for example, in the processes described in U.S. Pat. Nos. 7,479,290 and 7,078, 063 and European Patent Number EP00200229, concentrated or diluted ammonia is added until a pH of 8 to 10 is reached and the formation of precipitate is induced by heating which can be purified by silica gel chromatography, liquid-liquid extraction and/or crystallization processes. The final products are presented as dried extracts rich in Solasodine glycosides with purity greater than 60%.

Although several processes with different solvents and conditions for the extraction and purification of Saponins from *Solanum* genus plants are known, the efficiency of such processes described is still insufficient and the purity of the obtained extracts have not typically exceeded 80%.

The processes set forth as part of the present invention involves easier, more selective and more efficient extraction and purification processes for obtaining Solasodine glycosides from *Solanum* genus plants, using low-toxicity solvents. The processes of the invention utilize fruits of *Solanum* at any stage of maturation without the requirement of undergoing initial drying stages. A further advantage of the claimed processes is that the glycosides extraction can be performed at room temperature and its purification does not require complete evaporation of solvents, thus obtaining an extract having purity in excess of 92% at higher yields than previously reported such as greater than 1%.

SUMMARY OF THE INVENTION

In one aspect of the invention, a process for preparing a mixture of saponins in a solid phase comprising treating plants from the *solanum* genus with a liquid comprising a first alcohol to form a first alcohol solution and plant material; treating the plant material with a first liquid comprising an acid to form an acid solution; combining the acid solution with the first alcohol to get a combined solution; treating the combined solution with a base to obtain a resulting solid; treating the resulting solid with a third liquid comprising a second alcohol to obtain a second alcohol solution; and treating the second alcohol solution with a fourth liquid comprising a polarity modifying agent to form a mixture of saponins in a solid phase, is provided. In a further aspect of the invention, one or more saponins in the solid phase made by such a process is provided.

In an additional aspect of the invention, a solid phase of saponins is provided wherein at least 92% of the solid phase is saponins.

In a further aspect of the invention, a method of improving skin health or skin appearance comprising topically administering to a human a skincare composition comprising an effective amount of one or more saponins prepared according to the process of the first aspect of the invention are provided.

In yet an additional aspect of the invention, a method of improving skin health or skin appearance comprising topically administering to a human an effective amount of one or more saponins in a skincare composition wherein the one or more saponins are greater than 92% pure is provided.

In a further aspect of the invention, a cosmetic composition comprising one or more saponins and one or more cosmetically acceptable excipients is provided.

DETAILED DESCRIPTION OF THE INVENTION

Figure 1:
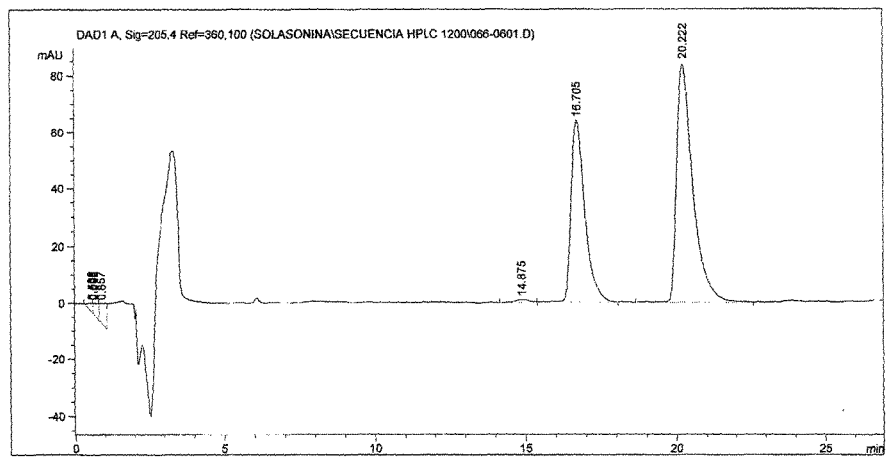
FIG. 1. HPLC-UV chromatographic profile of the dry glycoside rich extract obtained from *Solanum mammosum* in Example 1.

In many embodiments of the invention, processes for preparing a solid phase of one or more saponins are provided from fruits from *Solanum* genus plants. Embodiments of the invention include the processes as set forth herein and the solid phase of one or more saponins made by such processes. In these embodiments, the purity of the saponins obtained is greater than 92%. In these and other embodiments, the purity obtained is 93%, 94%, 95%, 96%, 97%, 98%, 99%, 99.5 or 99.9% or higher. Typically, the use of chromatographic separation is not required to achieve the purities so obtained.

In the embodiments of the invention, superior yields to prior art processes are also obtained. Such yields may be greater than 1% when compared to dry plant starting material and may be as high as 1.5% or more.

Any of the plants of the *Solanum* genus may be used according to the processes of these and other embodiments to provide such solid phases of saponins. For example, species of *Solanum* such as *Solanum agrarium, Solanum atropurpureum, Solanum betaceum, Solanum quitoense, Solanum crinitum, Solanum hirtum, Solanum marginatum, Solanum surattense Burm, Solanum lycocarpum, Solanum lycopersicum, Solanum macranthum, Solanum mammosum, Solanum melongena, Solanum nigrum, Solanum psychotrioides, Solanum sycophanta* and *Solanum xanthocarpum* may be used. In such embodiments, the plants may be pre-treated such as by shredding, grinding, chopping, or some combination thereof prior to undergoing such processes. Such pre-treatment may be used, for example, to increase the surface area of the plants used in the processes of the invention.

The saponins obtained in the solid phase may be any saponin that is found in the *solanum* genus. For example, such saponins include solamargine, solasonine, chaconine, solanidine, solanine, sycophantine, tomatine, and solasodine mono and/or diglycosides. In some embodiments, the saponins are alkaloidal saponins. In yet other embodiments, the saponins obtained are solasonine and solamargine. The solid phase of the saponins so obtained may be crystalline such as a white crystalline powder. Obtaining such crystalline saponins may be obtained, in some embodiments, by recrystallizing the saponins obtained in the solid phase. Such recrystallization may be done by conventional techniques in suitable crystallization solvents such as an aqueous alcohol solution. In these and other embodiments, recrystallization may yield purity of saponins which are 92%, 93%, 94%, 95%, 96%, 97%, 98%, 99%, 99.5%, 99.9% or higher. Identification of the saponins obtained according to processes of the invention may be done by one of number of standard chemical or analytical techniques.

Processes of the invention include preparing mixtures of saponins in the solid phase comprising multiple steps including treating plants from the *solanum* genus with a liquid comprising a first alcohol form a first alcohol solution and plant material. In some embodiments, the treatment with the first alcohol may take between about 36 to about 120 hours and may be filtered prior to further treatment. The time for treatment may be reduced by elevating the temperature, for example. Thus, in other embodiments, the amount of time may be less than 36 hours such as between 12 hours and 36 hours, or 12 hours and 24 hours or even less. The first alcohol may be, for example, a Class 3 alcohol as that term is used in the United States Pharmacopeia section on residual solvents which can be found, for instance, at USP 30<467> (Residual Solvents) and well understood to those of ordinary skill in the art. Such alcohols include, for example, ethanol, propanol, 1-butanol, 2-butanol, 3-methyl-1-butanol, isopropanol, isobutanol, pentanol, and a combination thereof. The liquid may be solvent and often such a solvent is water. In some embodiments, the first alcohol solution is ethanol and water. When the liquid is water, the concentration of the first alcohol, such as, for example, ethanol, in water, by volume, may be between about 5% and 99% including between about 10% and 90%, about 20% and about 80%, about 30% and about 75%, about 50% and 75%, about 60% and 75%, about 65% and 75% and including about 65%, 66%, 67%, 68%, 69%, 70%, 71%, 72%, 73%, 74% and 75%.

In an additional step, the plant material is treated with another liquid which liquid comprises an acid thus forming an acid solution. The liquid is typically a solvent and often such a solvent is water. Typical acids are weak acids such, as for example, acetic acid or other organic acids such as $C_2$-$C_5$ organic acids including propionic acid, butyric acid, and pentoic acid. In many embodiments, the acid is added until the pH of the acid solution is between about 1 and about 5 including about 3.5 and about 4.5, and, for example, including a pH of about 4. After the addition of the acid, the acid solution may be left to stand, agitated, or both. Prior to further treatment with a base, the acid solution may be filtered. In some embodiments, the acid solution is acetic acid and water. When the liquid is water, the concentration of the acid, such as acetic acid, in water, by volume, may be between about 1% and about 50% including between about 3% and about 30%, about 3% and about 20% including about 3%, 4%, 5%, 6%, 7%, 8%, 9%, 10%, 11%, 12%, 13%, 14%, 15%, 16%, 17%, 18%, 19% and 20%.

In a further step, the acid solution is combined with the first alcohol solution to make a combined solution. The combined solution may then be treated with a liquid comprising a base to form a resulting solid. Prior to the treatment, the combined solution may be optionally filtered. The liquid is typically a solvent and often such a solvent is water. Examples of bases include sodium hydroxide, potassium hydroxide, lithium hydroxide, ammonium hydroxide, sodium carbonate, potassium carbonate and ammonium carbonate. In many embodiments, the base is added until the pH of the acid solution increases to between about 8 and 14 including, for example, a pH of between about 10 and 13. Subsequent to basification, the resulting may optionally be washed with water prior to further treatment. When the liquid is water, the concentration of the base, such as sodium hydroxide, in water, by volume, may be between about 1% and 30% including between about 5% and about 20%, about 5% and 15%, and including about 5%, 6%, 7%, 8%, 9%, 10%, 11%, 12%, 13%, 14%, and 15%. The resulting solid may be re-treated with an acid solution, an alcohol solution, and followed by a base in solution to increase the purity of the resulting solid. The alcohol solution can be the same composition or different than the first alcohol solution. The acid solution for the re-treatment can be of the same or different composition than the acid solution previously used. The base in solution for the pre-treatment can be of the same or of different composition than the base used previously.

In a further step, the resulting solid is treated with a liquid comprising a second alcohol so as to result in a second alcohol solution. The liquid is typically a solvent and often such a solvent is water. The second alcohol may be the same as the first alcohol or different and may be at a different concentration than the first alcohol solution. Optionally, the second alcohol solution is heated, such as to about 45° C. to about 55° C. when the second alcohol is ethanol, and hot filtered prior to further treatment. The second alcohol may be, for example, a Class 3 alcohol as that term is used in USP 30<467> (Residual Solvents) and well understood to those of ordinary skill in the art. Such alcohols include, for example, ethanol, propanol, 1-butanol, 2-butanol, 3-methyl-1-butanol, isopropanol, isobutanol, pentanol, and a combination thereof and second alcohol is selected from the group consisting of ethanol, propanol, 1-butanol, 2-butanol, 3-methyl-1-butanol, isopropanol, isobutanol, pentanol, or a combination thereof. In some embodiments, the second alcohol solution is ethanol and water. When the liquid is water, the concentration of the second alcohol, such as, for example, ethanol, in water may be between about 5% and about 99% including between about 20% and about 99%, about 50% and about 99%, about 70% and about 99%, about 85% and about 99% and including about 85%, 86%, 87%, 88%, 89%, 90%, 91%, 92%, 93%, 94%, 95%, 96%, 97%, 98% and 99%.

In an additional step, the second alcohol solution is treated with a liquid comprising a polarity modifying agent to form a mixture of saponins in the solid phase. The liquid is typically a solvent and often such a solvent is water. Prior to treatment with the polarity modifying agent, the second alcohol solution may optionally be heated or filtered or both. The polarity modifying agent is a material that is capable of modifying the polarity of the liquid in which it is placed so as to promote the formation of solid phase saponins Examples of polarity modifying agents include inorganic salts. Such inorganic salts include sodium chloride, potassium chloride, ammonium chloride, sodium sulfate, potassium sulfate, ammonium sulfate, sodium phosphate, potassium phosphate and ammonium phosphate, and mixtures thereof. The concentration of the polarity modifying agent, such as, for example, sodium chloride, in water, measured as weight per volume, may be between about 1% and about 50% including between about 1% and about 25%, about 5% and about 20%, about 5% and about 15%, including about 5%, 6%, 7%, 8%, 9%, 10%, 11%, 12%, 13%, 14%, and 15%.

The solid phase saponins so obtained from the polarity modifying agent can filtered and/or redissolved in an alcohol-water solution wherein the alcohol is a Class 3 alcohol and recrystallized such as, for example, by cooling or other known techniques in the art. Examples of such alcohols include, for example, ethanol, propanol, 1-butanol, 2-butanol, 3-methyl-1-butanol, isopropanol, isobutanol, pentanol, and a combination thereof and second alcohol is selected from the group consisting of ethanol, propanol, 1-butanol, 2-butanol, 3-methyl-1-butanol, isopropanol, isobutanol, pentanol, or a combination thereof. When the alcohol is ethanol, the concentration of the alcohol in water, for example can be between about 80% and about 99% including between about 85% and about 97%, about 90% to about 96%, including about 90%, 91%, 92%, 93%, 94%, 95%, and 96% by volume. Resulting crystals may be isolated by filtration and dried to yield solid phases saponins.

In many embodiments of the invention, the processes used to prepare the solid phase of saponins do not use any Class 1 or Class 2 solvents as those terms are understood by those of ordinary skill in the art as set forth in USP 30<467> (Residual Solvents). Such Class 1 and Class 2 solvents include, for example, chloroform and other halogenated solvents. As a result, resulting solid phase saponins so prepared contain are substantially free of or contain no detectable Class 1 or Class 2 solvents such as chloroform or other halogenated solvents. In these and other embodiments, ammonia is not used in the processes of the invention. Thus, in such embodiments, resulting solid phase saponins so prepared are substantially free of or contain no detectable ammonia.

Various additional operations or steps may also be used in many embodiments of processes of the invention. External heat, for example, may be applied to aid in dissolution, however, in other embodiments, no such heat is added. In these and other embodiments, evaporating liquids such as solvents to dryness to assist in the isolation of solids, however, in other embodiments, not such evaporating to dryness is performed. Flocculents may also be used during the process to assist in the removal of insolubles. Alum is an example of such a flocculent.

In some embodiments, fruits of one or several *Solanum* genus of plants undergo an extraction process using an alcohol solution of 50% to 90% (v/v) in a 1:1, 1:2 or 1:3 ratio. After between about 36 and 120 hours, the liquid phase of the plant mass may be filtered off. The obtained plant mass may then be subject to extraction using, for example, an aqueous acid solution of 5% to 10% (v/v), such as with acetic acid, until a pH value between 3 and 5 is reached. It may then be allowed to stand for 36 to 120 hours, further filtered to recover the liquid acidic phase and discard the solid phase. The liquid acidic phase (the acid solution) may be combined with the previously obtained alcohol solution and insoluble impurities may be removed by centrifugation or decantation, followed by addition of a strong base in solution (such as NaOH in water) until a pH between 10 and 12 is reached and constant stirring may be used to help obtain a precipitate, which may be further separated and sufficiently washed with water until it becomes reddish brown solid (precipitate A).

Precipitate A may be dissolved in an alcohol solution until a minimal presence of solid material in suspension is noticed. Subsequently, this solution may be heated to a temperature between 45° C. and 55° C., after reaching said temperature, the solution may be filtered while still hot to remove insoluble impurities and then allowed to stand until it reaches room temperature. The solid phase of the liquid may then removed by filtration and the solid discarded. A polarity modifying agent may added to the obtained solution in order to form two phases (solid+liquid), wherein the solid (precipitate B) is recovered.

The obtained precipitate B may be re-dissolved in a an alcohol solution (e.g., 90% to 96% v/v), which may be heated until the solution reaches the saturation point and is then allowed to cool to room temperature, in order to allow the formation of crystals, which can be further separated by filtration. The retained product may be dried to obtain saponins in the solid phase.

Additional embodiments of the invention include cosmetic compositions such as skincare compositions made from solid phase saponins and methods of improving skin care health with such skincare compositions. Such saponins may be made according to the processes of the invention. Examples of saponins which may be used include solamargine, solasonine, chaconine, solanidine, solanine, sycophantine, tomatine, solasodine monoglycosides and solasodine diglycoside. In some embodiments, the saponins are solasonine and solamargine. The saponins in the cosmetic compositions of the invention are typically of purity greater than 92% including 93%, 94%, 95%, 96%, 97%, 98%, 99%, 99.5, 99.9% or greater. The saponins may be obtained from any plant of the *solanum* genus including, for example, *Solanum agrarium, Solanum atropurpureum, Solanum betaceum, Solanum quitoense, Solanum marginatum, Solanum surattense Burm, Solanum crinitum, Solanum hirtum, Solanum lycocarpum, Solanum lycopersicum, Solanum macranthum, Solanum mammosum, Solanum melongena, Solanum nigrum, Solanum psychotrioides, Solanum sycophanta* and *Solanum xanthocarpum*. In particular, the saponins may be sourced from *solanum mammosum* or *solanum agragium* or both.

The cosmetic compositions, such as skincare compositions, of the invention additionally comprise one or more cosmetically acceptable excipients. Such excipients may include solvents, sequestrants, humectants, thickening agents, emulsifiers, emollients, absorbing agents, preservatives, fragrances, antioxidants, pH modifiers, texturizing agents, vitamins, skin conditioners, skin protectants, antioxidants, buffers, surfactants, solvents, astringents, antimicrobials, antiestatic compounds, keratolytic compounds, binders, film forming agents, solvents, and combinations thereof.

In many embodiments, the cosmetic compositions, such as for skincare compositions include skin conditioners, skin protectants, humectants, antioxidants, buffering agents, surfactants, emulsifying agents, solvents, astringents, antimicrobial agents, antistatic agents, keratolytic agents, preservatives, binders, viscosity controlling agents, and film forming agents.

The ingredients of a cosmetic composition for skincare compositions may have more than one function. For example, one such class combines skin conditioning, skin protection, humectant, and antioxidant properties. Excipients falling within this class shall be termed "Class A Excipients". Examples of Class A Excipients include Algae extract, *carica papaya* fruit juice, aloe vera, *cocos nucifera* fruit juice, hydrolyzed collagen, and victoria amazonica leaf extract. In cosmetic compositions of the invention including skincare compositions of the invention, the amount of the excipients used within said class may vary between about 0.1% and about 15% of the overall composition by mass. Such amounts may further include between about 1% and about 10%, about 2% and about 8%, about 3% and about 7%, about 4% and about 6% including about 5%. Such excipients may be a single excipient within the class or a combination of excipients within the class. In one particular embodiment, aloe vera is used within this class as a single excipient.

In another class, the functions of skin conditioning and antioxidant are combined. Excipients falling within this class shall be termed "Class B Excipients". Examples of Class B Excipients include aminopropyl tocopheryl phosphate, ascorbic acid, *capsicum annuum* fruit extract, carotenoids, hydrolyzed olive fruit extract, and vitamin E. In cosmetic compositions of the invention including skincare compositions of the invention, the amount of the excipients used within said class may vary between about 0.1% and about 5% of the overall composition by mass. Such amounts may further include between about 0.1% and about 1%, about 0.2% and about 0.8%, about 0.3% and about 0.7%, about 0.4% and about 0.6%, including about 0.5%. Such excipients may be a single excipient within the class or a combination of excipients within the class. In one particular embodiment, vitamin E is used within this class as a single excipient.

In yet another class, the functions of buffering, surfactant, and emulsifier are combined. Excipients falling within this class shall be termed "Class C Excipients". Examples of Class C Excipients include triethanolamine, acetic acid, ammonia, citric acid, ethyl ethanolamine, and phosphoric acid. In cosmetic compositions of the invention including skincare compositions of the invention, the amount of the excipients used within said class may vary between about 0.5% and about 2.5% of the overall composition by mass. Such amounts may further include between about 1% and about 2.5%, about 2% and about 2.5%, including at about 2.1%, 2.2%, 2.3%, and 2.4%. Such excipients may be a single excipient within the class or a combination of excipients within the class. In one particular embodiment, triethanolamine is used within this class as a single excipient.

In an additional class, the functions of solvent, astringent, and antimicrobial are combined. Excipients falling within this class shall be termed "Class D Excipients". Examples of Class D Excipients include ethanol, denatured alcohol, propyl alcohol, propanediol, and t-butyl alcohol. In cosmetic compositions of the invention including skincare compositions of the invention, the amount of the excipients used within said class may vary between about 0.5% and about 3% of the overall composition by mass. Such amounts may further include between about 1% and about 3% as well as between about 2% and about 3% including about 3%. Such excipients may be a single excipient within the class or a combination of excipients within the class. In one particular embodiment, ethanol is used within this class as a single excipient.

In a further class, the functions of antistatic agents, buffers, humectants, and skin conditioners are combined. Excipients falling within this class shall be termed "Class E Excipients". Examples of Class E Excipients include urea, 3-lauryl/tridecylglyceryl ascorbate, dimethicone, and paraffinum liqiudum. In cosmetic compositions of the invention including skincare compositions of the invention, the amount of the excipients used within said class may vary between about 3% and about 10% of the overall composition by mass. Such amounts may further include between about 3% and about 8%, about 4% and about 7%, about 5% and about 6%, including about 5% and about 6%. Such excipients may be a single excipient within the class or a combination of excipients within the class. In one particular embodiment, urea is used within this class as a single excipient.

In yet another class, the functions of a keratolytic agent, skin conditioner, and preservative are combined. Excipients falling within this class shall be termed "Class F Excipients". Examples of Class F Excipients include salicylic acid, chloroacetic acid, sodium lactate, thiosalicylic acid, ammonium lactate, and tamarindus indica extract. In cosmetic compositions of the invention including skincare compositions of the invention, the amount of the excipients used within said class may vary between about 0.5% and about 2% of the overall composition by mass. Such amounts may further include between about 0.5% and about 1.5%, about 0.8% and about 1.2%, including at about 0.8%, 0.9%, 1%, 1.1%, and 1.2%. Such excipients may be a single excipient within the class or a combination of excipients within the class. In one particular embodiment, salicylic acid is used within this class as a single excipient.

The cosmetic compositions, including skincare compositions, of the invention may further include the following three classes—binders/viscosity controlling agents/film formers such as sodium acrylates copolymers; emollients/skin protecting agents/solvent such as paraffinum liquidum; and skin conditioning/surfactants such as PPG-1 Trideceth-6. The combination of these three classes is typically between about 0.5% and about 5%, including between about 1% and about 4%, about 2% and 4% including about 3%. These three classes may be sourced as a single material such as SALCARE® SC91 which is commercially available from BASF.

The cosmetic compositions, including skincare compositions, of the invention may further include water at between about 57% and about 95% of the total composition. The amount of water can also vary between about 60% and about 90%, about 70% and about 85%, including about 80%.

The cosmetic compositions, including skincare compositions, may contain any of a number of saponins from 0.001% to about 10.0% including between about 0.001% and about 5%, about 0.005% and about 2%, about 0.005% and about 1.5%, about 0.005% and about 1.0%, about 0.005% and about 0.5%, about 0.005% and about 0.25%, about 0.005% and about 0.20%, about 0.005% and about 0.15%, about 0.005% and about 0.1%, about 0.005% and about 0.05%, about 0.005% and about 0.025%, about 0.008% and about 0.021% including about 0.1% and about 0.2%. Such saponins may be made according to the processes of the invention and may include solamargine, solasonine, chaconine, solanidine, solanine, sycophantine, tomatine, and solasodine mono and/or diglycosides. In many embodiments, the saponins are solasonine and solamargine combined and may range each from about 0.001% to about 5%, about 0.001% and about 2%, about 0.001% and about 1.5%, about 0.005% and about 1.0%, about 0.005% and about 0.5%, about 0.005% and about 0.25%, about 0.005% and about 0.15%, about 0.005% and about 0.1%, about 0.005% and about 0.05%, about 0.005% and about 0.025%, about 0.008% and about 0.015% and including about 0.01%.

It is common in the cosmetics industry to use parabens as preservatives. Such parabens are controversial because of concerns about their health effects. In many embodiments of the invention no parabens or other preservatives are added to the cosmetic compositions.

The dosages forms of the cosmetic compositions, such as skincare compositions, include any suitable dosage form. Specifically, such forms include, cream, gel, cream-gel, emulsion, compact powder, solution, and suspension.

The skincare compositions of the invention may be used to improve skin health or skin appearance by reducing the appearance of wrinkles and fine expressions on the face, back, chest, and hands. The skincare compositions may be used to improve skin texture. The skincare compositions may also be used to remove withered skin cells so as to allow for better nutrition and hydration. The skincare compositions may further be used to reduce the damage caused by free radicals and other environmental factors on the skin and prevent premature skin aging. The skincare compositions may further be used to form a protective skin barrier to revitalize, nourish and hydrate the skin. The skincare compositions further promote keeping an even skin tone.

EXAMPLES

Example 1

Obtaining a Dry Extract from *Solanum mammosum*

Approximately 6 kilograms of fresh and ripe fruits of *S. mammosum* were ground in 20 liters of an ethanol-water (70% v/v) solution. The immersed plant material in the ethanol-water solution was stirred and left for digestion during 80 hours at room temperature. Once the digestion time was completed, the plant material was separated from the ethanol-water solution by filtration. The trapped plant material in the filter medium was mixed with a solution of 12% v/v acetic acid until a pH of 4 was reached, followed by stirring at room temperature. After 120 hours of acid digestion passed, the solution was filtered, the plant material was discarded and the supernatant was stored in a glass container for further processing.

The ethanol-water and acid solutions obtained in the preceding phases were mixed and homogenized at room temperature. The insoluble contaminating material was separated by centrifugation at 4000 rpm for 10 min. The obtained solution after centrifugation was mixed and stirred at room temperature with sufficient sodium hydroxide (10% v/v) until a pH value of 10 was reached. A brown precipitate was obtained, which was mixed and stirred with sufficient water at room temperature. Once the separation of a liquid and solid phase (precipitate) was clearly defined, the latter was separated from the liquid by decantation. This process was repeated 5 times, obtaining a brown precipitate (precipitate A).

Precipitate A was mixed with sufficient ethyl alcohol (96% v/v) until complete dissolution was reached, with a minimal presence of solid material in suspension. The obtained solution was heated and stirred until a temperature of 50° C. Immediately, the solution was hot filtered to remove unwanted insoluble impurities.

The obtained liquid in the previous step was mixed and stirred at room temperature with a polarity modifying solvent, a NaCl 10% w/v salt solution. The insoluble white solid (precipitate B) obtained after the addition of the polarity modifying solvent in the medium was recovered by filtration. The retained solid was re-dissolved in a 96% (v/v) ethyl alcohol solution and concentrated by solvent evaporation.

After turbidity of the solution was observed, the solution was left at rest to obtain the glycosides of interest via crystallization. The obtained crystals are separated by filtration, dried at room temperature and ground to a fine white powder, with high purity and rich in Solasodine glycosides, which was stored in containers under appropriate conditions to ensure stability. 15.5 grams of dry extract was obtained, giving a yield of 0.26%. Table 1 shows the yield and purity of the dry extract obtained.

TABLE 1

| % Yield | Purity (HPLC-MS Analysis) | | |
|---|---|---|---|
| (Wet base) | % Solasonine | % Solamargine | % Total Purity |
| 0.26 | 40.3 | 58.0 | 98.3 |

Example 2

Qualitative and Quantitative Identification of the Compounds within the Extract of Example 1

In order to determine the presence of the Solasodine glycosides, 100 mg of precipitate A from Example 1 was weighed and dissolved in 15 mL of a 10% acetic acid solution. The solution was divided into three fractions of 5 mL and 5 drops of Dragendorff, Mayer and Wagner reagents were added to each fraction. The results are illustrated in Table 2.

TABLE 2

| REAGENT | OBSERVATION | RESULT |
|---|---|---|
| Dragendorff | Formation of an orange-reddish colored precipitate | Positive for Solasodine glycosides |
| Mayer | Formation of a cream colored precipitate | Positive for Solasodine glycosides |
| Wagner | Formation of a brown-reddish color precipitate | Positive for Solasodine glycosides |

With the use of High Performance Liquid Chromatography (HPLC) and Mass Spectrometry (MS), the major components of the extract obtained in Example 1 were identified. Identification and quantification of the purity of the Solasonine sample was carried out in a HPLC chromatograph with an Agilent 1100 quaternary pump, UV detector and RP-18 250 mm×4.6 mm×5.0 um Alltech® column. The mobile phase used was acetonitrile/phosphate buffer 36.5:63.5 with an isocratic mode of 1.0 mL/min. A Solasonine standard of 95.18% purity (Chengdu Biopurify Phytochemicals LTD) was used.

The identification and estimation of the compounds was supplemented with HPLC (MS) in an Agilent 1200 liquid chromatograph with a RP-18 250 mm×4.6 mm×5.0 um Alltech column. The mobile phase used was a mixture of water/acetonitrile/Isopropanol 94.5:5:0.5 with an isocratic flow of 1.0 mL/min. The mass detector was configured in positive ionization mode with a mass range from 100-1500 m/z.

Figure 2:
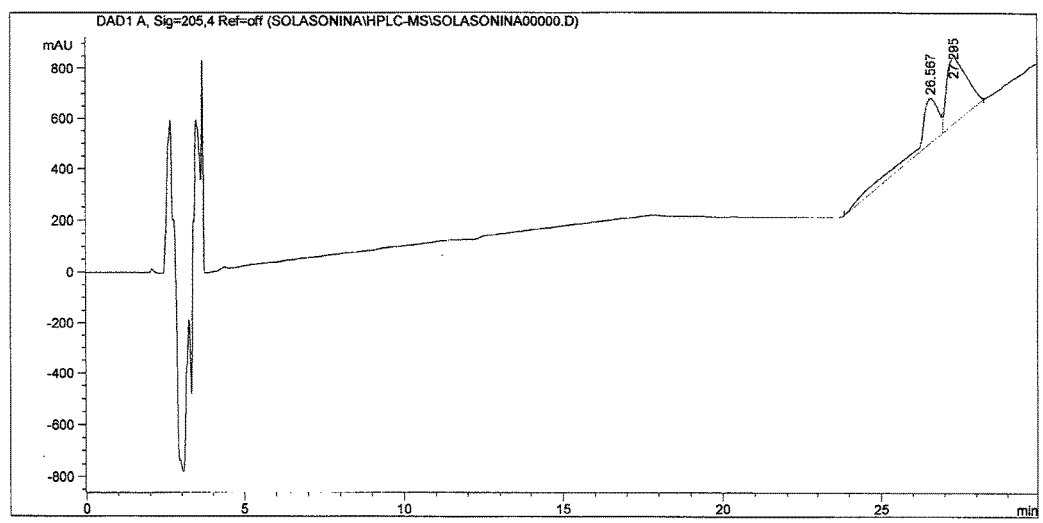
FIG. 2. HPLC-DAD-MS chromatographic profile of the dry extract obtained in Example 1.

FIG. 1 illustrates the HPLC-UV chromatographic profile of the sample. One of the peaks shown in this figure corresponds to Solasonine, which has an area ratio of 40.3% in the retention time (Rt)=16.705 min. The other peak with retention time (Rt)=20.222 min and an area ratio of 58.0%, corresponds to Solamargine. FIG. 2 shows the chromatographic profile by HPLC-DAD-MS.

Figure 3:
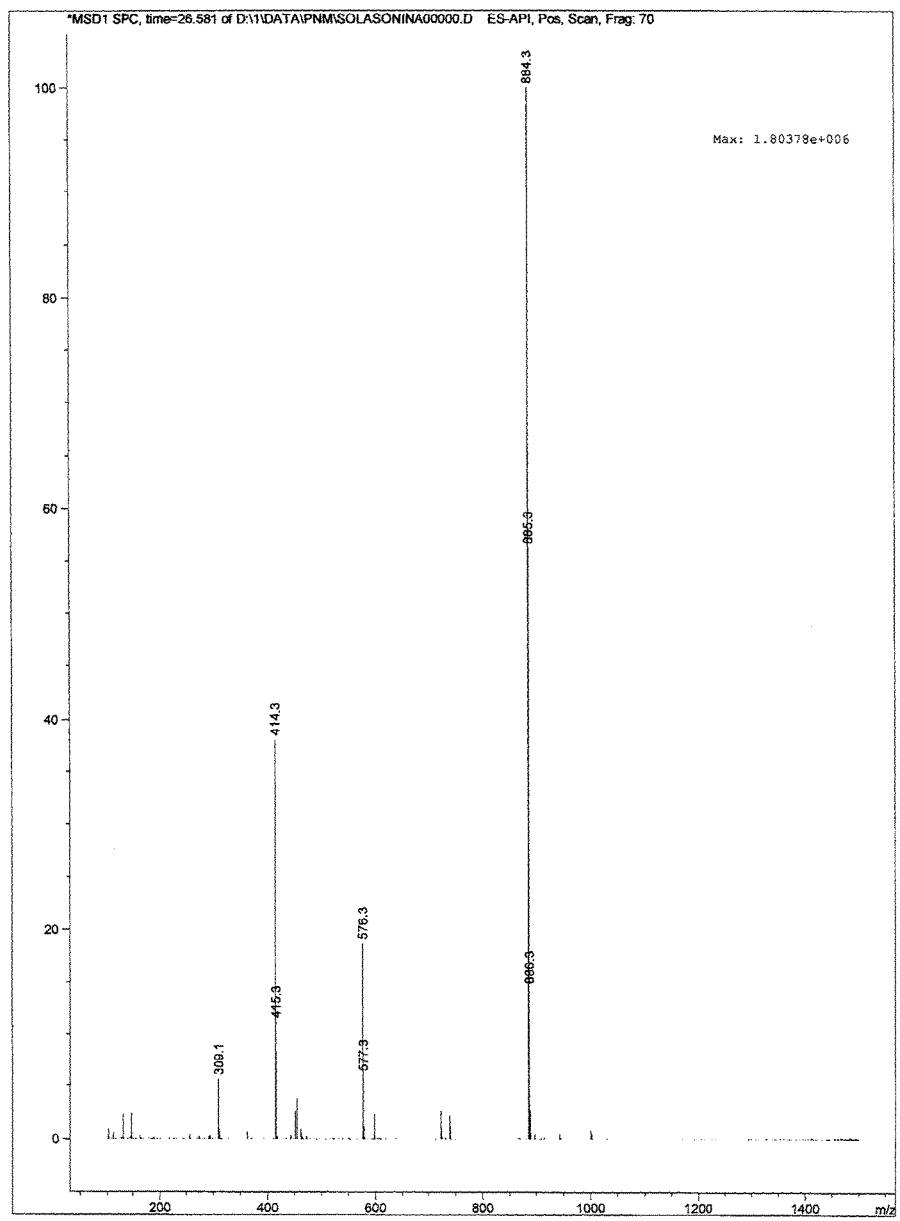
FIG. 3. Fragmentation profile of the compound with retention time (Rt=26.5 min) of the dry extract obtained in Example 1.
Figure 4:
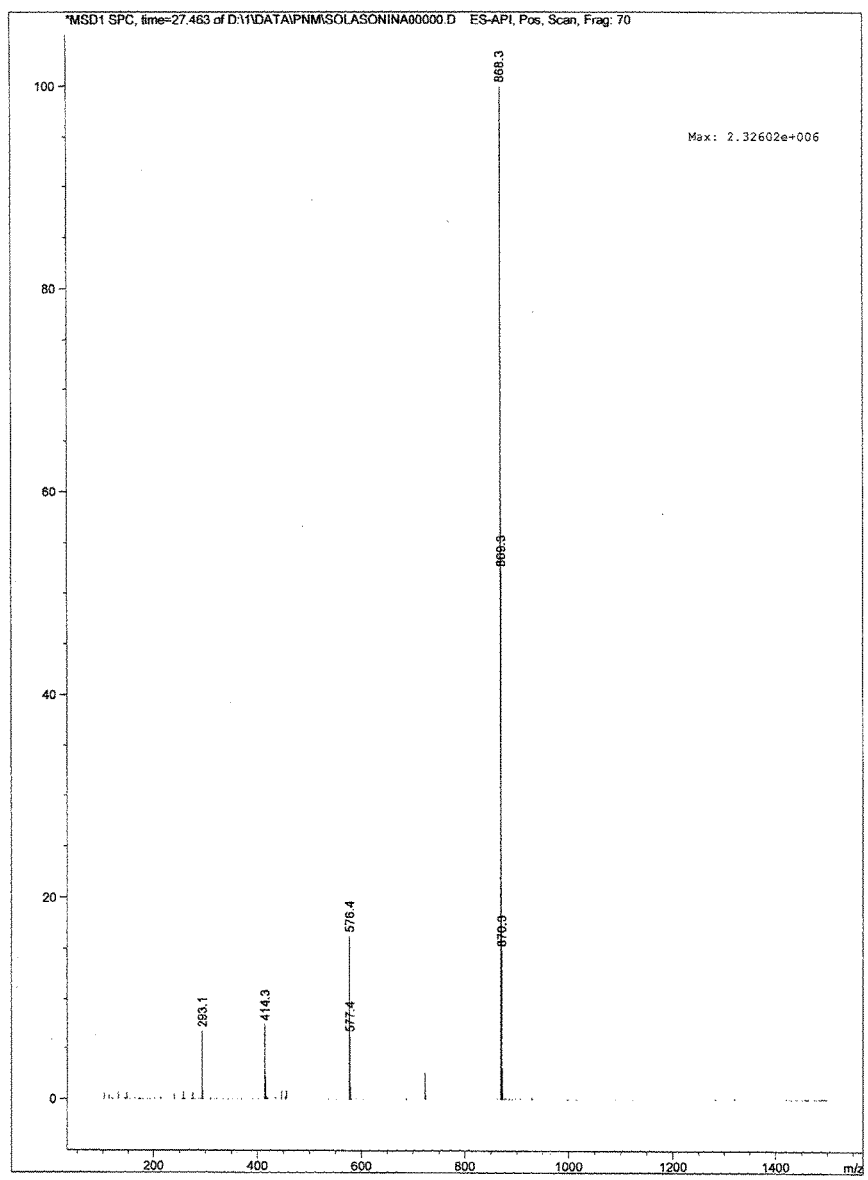
FIG. 4. Fragmentation profile of the compound with retention time (Rt=27.5 min) of the dry extract obtained in Example 1.

The first compound (Rt=26.5 min) corresponds to Solasonine, while the second compound (Rt=27.5 min) was identified as Solamargine, based on analysis of fragmentation profiles illustrated in FIG. 3 and FIG. 4, respectively.

Example 3

A Second Batch of Saponins from *Solanum mammosum*

Following the procedures of Example 1 generally, a second dry extract from *Solanum mammosum* was prepared. 81.2 grams of dry extract was obtained, giving a yield of 1.055%.

Example 4

Qualitative and Quantitative Identification of the Compounds within the Extract of Example 1

The saponins obtained in Example 3 were analyzed by electrospray ionization mass spectrometry. Samples were prepared by diluting 20.4 milligrams of the saponins from Example 3 in and dissolving in 10 mL of a 50/50 mix of ethanol-water. The samples were analyzed by an LC/MS system (Agilent Technologies Zorbax Eclipse XDB-C18 column, 4.6×150 mm). The mobile phases used were A (0.1% formic acid) and B (94.5%-acetonitrile; 5%-isopropanol; 0.5%-0.1% formic acid). The following gradient was used:

T=0 A-80% B-20%
T=14 A-70% B-30%
T=20 A-70% B-30%
T=27 A-40% B-60%
T=30 A-10% B-90%

Figure 5:
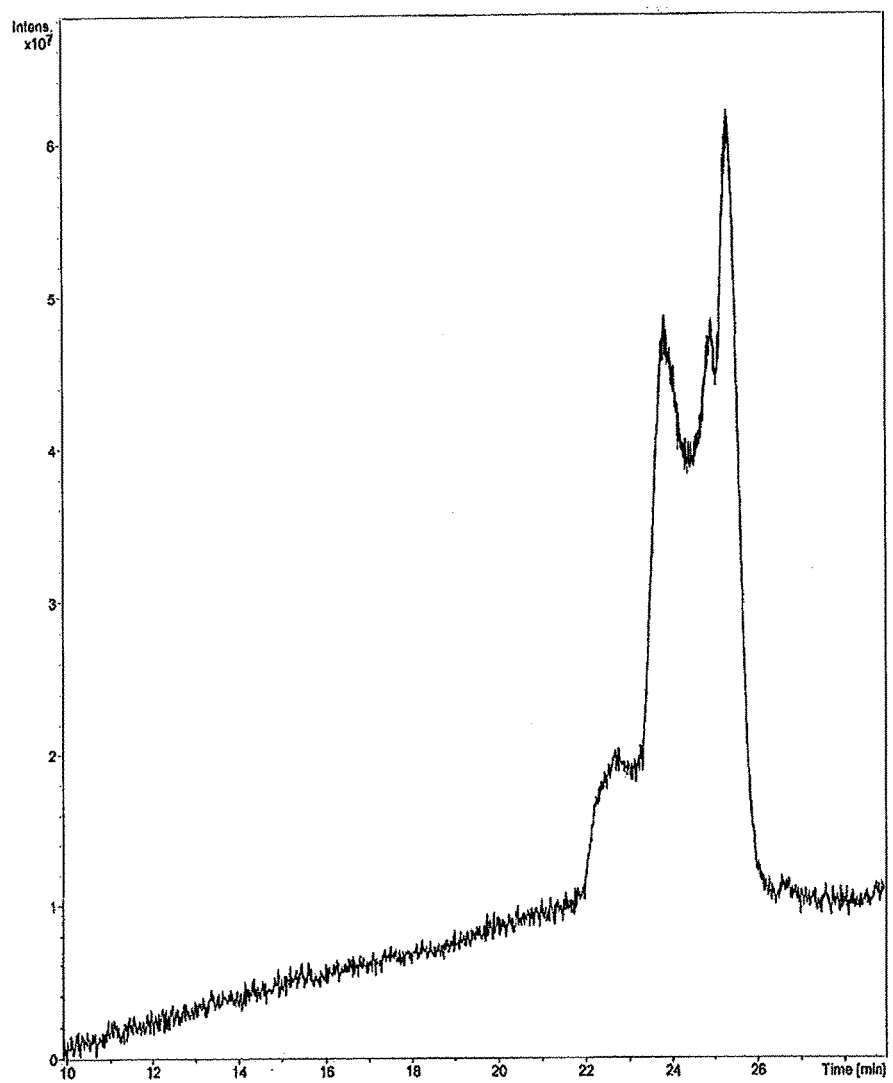
FIG. 5. Total ion count MS chromatogram from the sample obtained in Example 3 as a function of time FIG. 6. The mass spectrum at 22.1-22.9 minutes from FIG. 5.
Figure 6:
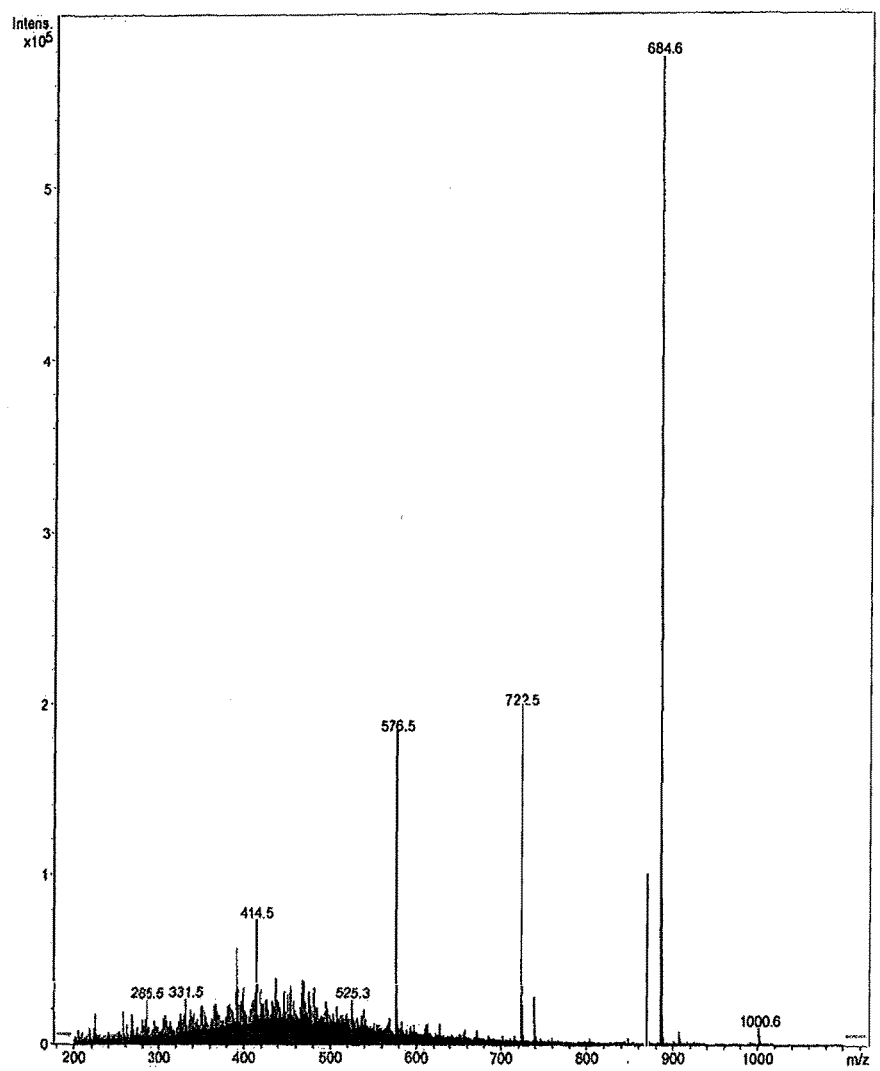
Figure 7:
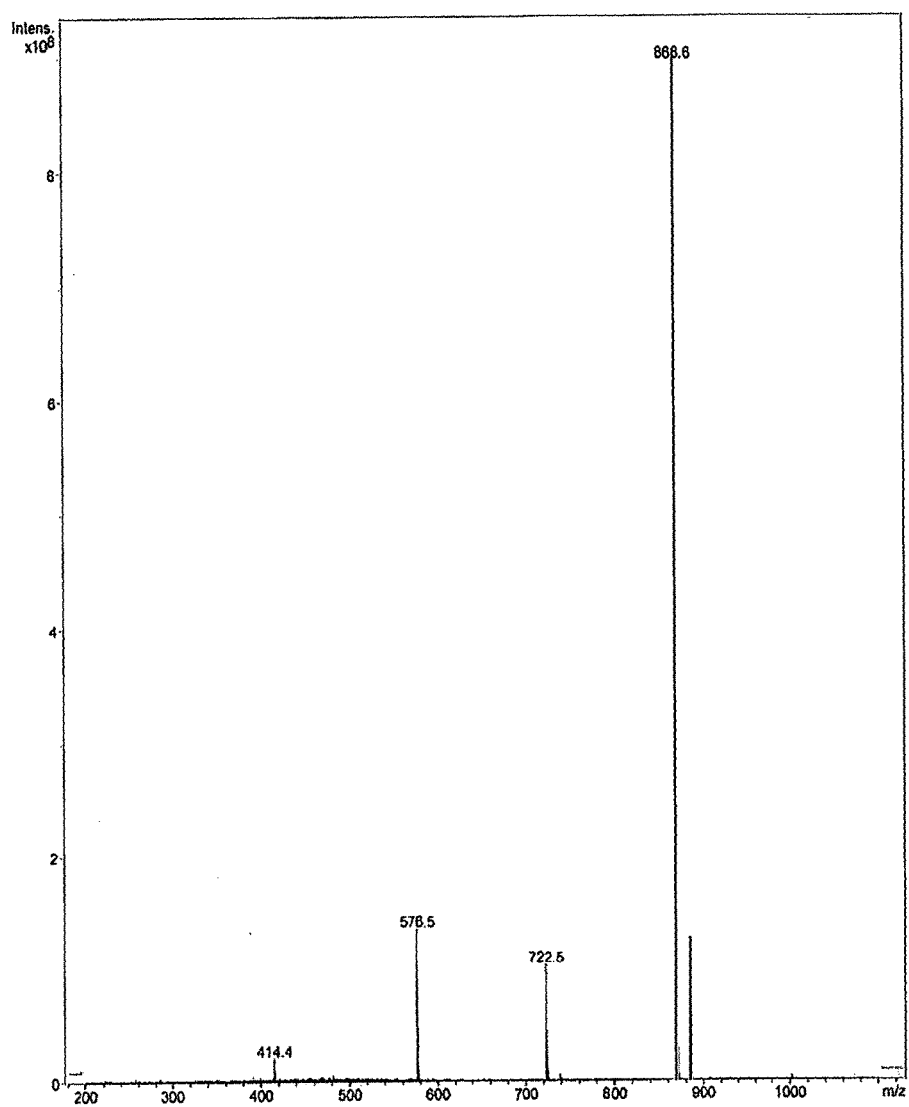
FIG. 7. The mass spectrum at 23.6-24.2 minutes from FIG. 5.
Figure 8:
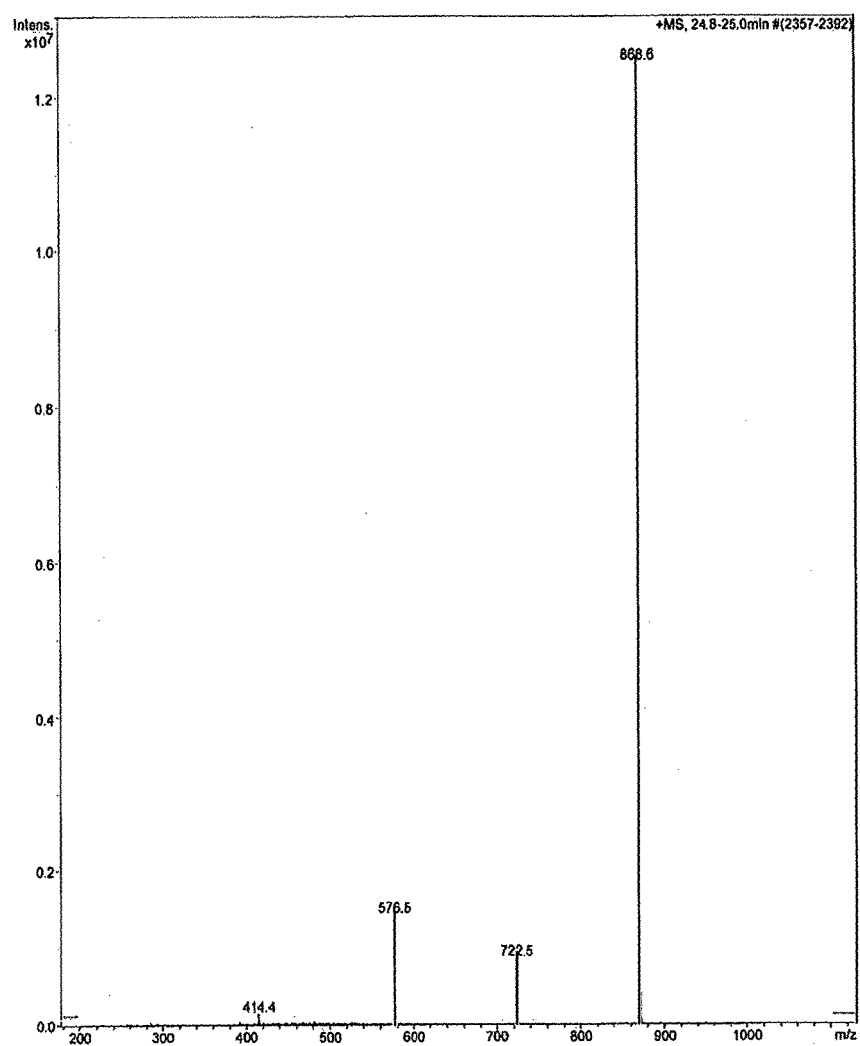
FIG. 8. The mass spectrum at 24.8-25.0 minutes from FIG. 5
Figure 9:
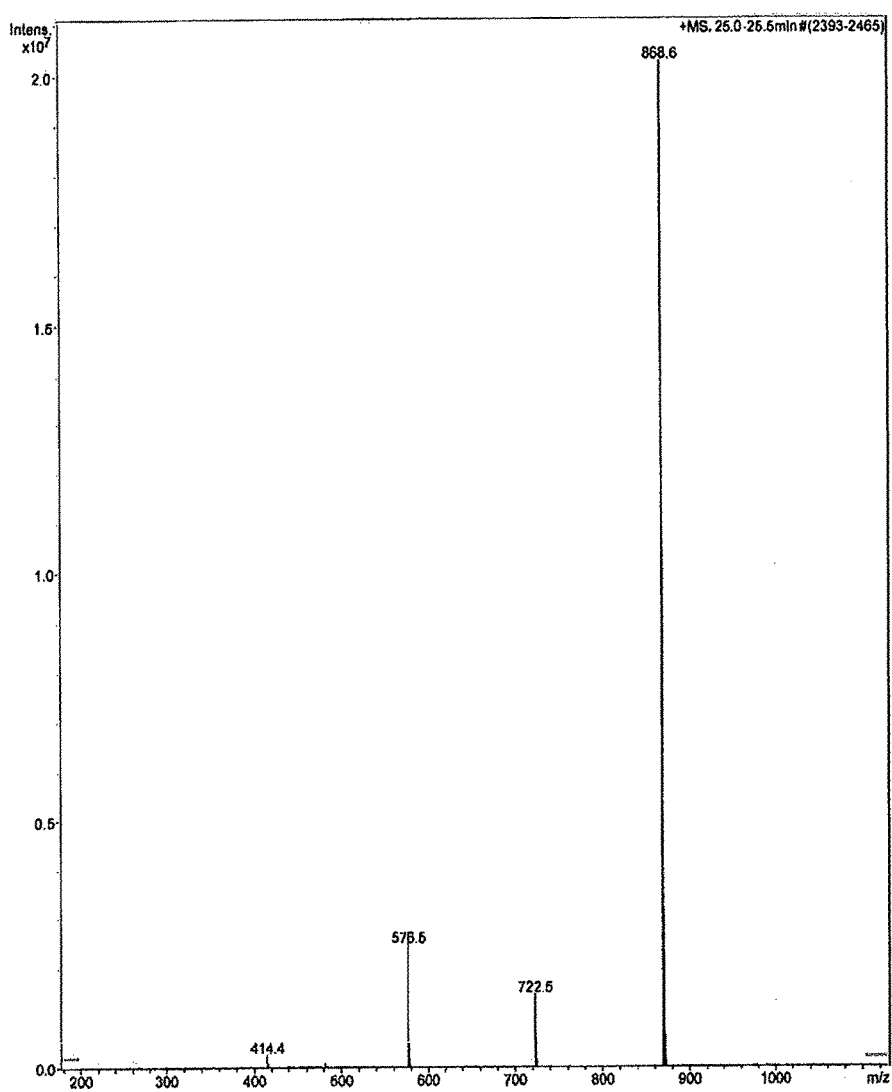
FIG. 9. The mass spectrum at 25.0-25.5 minutes from FIG. 5.
Figure 10:
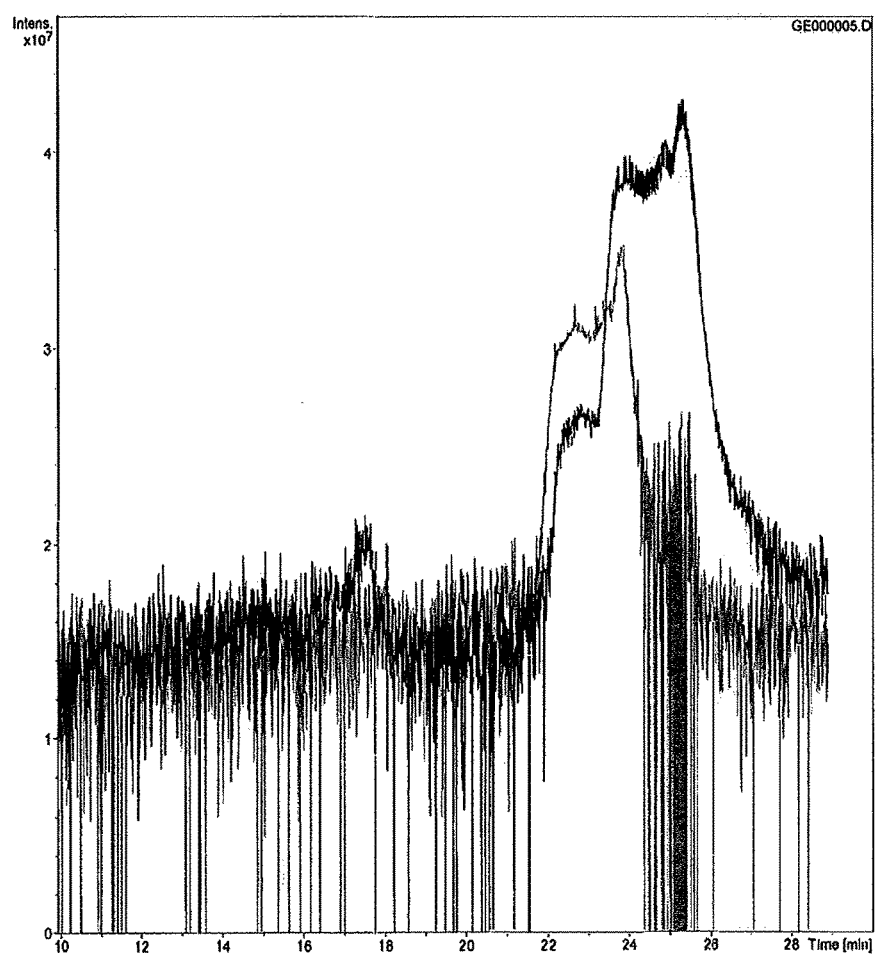
FIG. 10. Ion count for (M+H)+ ions at m/z 868 and m/z 884 from the sample obtained in Example 3 as a function of time.

FIG. 5 is the total ion count spectrum from the system with FIGS. 6-9 being mass spectral measurements taken at various different elution times as indicated on the spectra in the respective figures. The spectra showed two primary components having (M+H)+ ions at m/z 868 and m/z 884 indicative of components having a molecular weights of 867 and 883 respectively. By visual inspection of the mass spectral data it is apparent that the samples are of high purity. The individual ions, m/z 868 and 884, were both plotted as a function of retention in FIG. 10 with the y-axis representing ion counts. Using a trapezoidal measurement approach, an area count of $4.75 \times 10^7$ for m/z 868 (the signal having a peak maximum at about 25.5 minutes) and $2.24 \times 10^7$ for m/z 884 (the signal having a peak maximum at about 24 minutes) was estimated. Comparison of the area counts with the mass spectra and chromatographic data from Example 1 (and using the Example 1 data for reference) were used to estimate a purity of greater than 98%.

Example 5

Obtaining a Dry Extract from *Solanum agrarium*

Approximately 7 kilograms of fresh and ripe fruits of *S. agrarium* were ground in 20 liters of an ethanol-water (70% v/v) solution. The immersed plant material in the ethanol-water solution was stirred and left for digestion during 80 hours at room temperature. Once the digestion time was completed, the plant material was separated from the ethanol-water solution by filtration. The trapped plant material in the filter medium was mixed with a solution of 12% v/v acetic acid until a pH of 4 was reached, followed by stirring at room temperature. After 120 hours of acid digestion passed, the solution was filtered, the plant material was discarded and the supernatant was stored in a glass container for further processing.

The ethanol-water and acid solutions obtained in the preceding phases were mixed and homogenized at room temperature. The insoluble contaminating material was separated by centrifugation at 4000 rpm for 10 min. The obtained solution after centrifugation was mixed and stirred at room temperature with sufficient sodium hydroxide (10% v/v) until a pH value of 10 was reached. A brown precipitate was obtained, which was mixed and stirred with sufficient water at room temperature. Once the separation of a liquid and solid phase (precipitate) was clearly defined, the latter was separated from the liquid by decantation. This process was repeated 5 times, obtaining a brown precipitate (precipitate A).

Precipitate A was mixed with sufficient ethyl alcohol (96% V/V) until complete dissolution was reached, with a minimal presence of solid material in suspension. The obtained solution was heated and stirred until a temperature of 50° C. Immediately, the solution was hot filtered to remove unwanted insoluble impurities.

The obtained liquid in the previous step was mixed and stirred at room temperature with a polarity modifying solvent, a NaCl 10% w/v salt solution. The insoluble white solid (precipitate B) obtained after the addition of the polarity modifying solvent in the medium was recovered by filtration. The retained solid was re-dissolved in a 96% (v/v) ethanol-water solution and concentrated by solvent evaporation.

After turbidity of the solution was observed, the solution was left at rest to obtain the glycosides of interest via crystallization. The obtained crystals are separated by filtration, dried at room temperature and ground to a fine white powder, with high purity and rich in Solasodine glycosides, which was stored in containers and appropriate conditions to ensure stability. 92.0 grams of dry extract was obtained, giving a yield of 1.314% of saponins.

Example 6

Qualitative and Quantitative Identification of the Compounds within the *S. agrarium* Extract In order to determine the presence of the Solasodine glycosides, 100 mg of precipitate A from Example 3 (based on the procedure of Example 1) was weighed and dissolved in 15 mL of a 10% acetic acid solution. The solution was divided into three fractions of 5 mL and 5 drops of Dragendorff, Mayer and Wagner reagents were added to each fraction. The results are illustrated in Table 3:

TABLE 3

| REAGENT | OBSERVATION | RESULT |
|---|---|---|
| Dragendorff | Formation of an orange-reddish colored precipitate | Positive for Solasodine glycosides |
| Mayer | Formation of a cream colored precipitate | Positive for Solasodine glycosides |
| Wagner | Formation of a brown-reddish color precipitate | Positive for Solasodine glycosides |

The saponins obtained in Example 5 were analyzed by electrospray ionization mass spectrometry. Samples were prepared by diluting 20.4 milligrams of the saponins from Example 5 in and dissolving in 10 mL of a 50/50 mix of ethanol-water. The samples were analyzed by an LC/MS system (Agilent Technologies Zorbax Eclipse XDB-C18 column, 4.6×150 mm). The mobile phases used were A (0.1% formic acid) and B (94.5%-acetonitrile; 5%-isopropanol; 0.5%-0.1% formic acid). The following gradient was used:

T=0 A-80% B-20%
T=14 A-70% B-30%
T=20 A-70% B-30%
T=27 A-40% B-60%
T=30 A-10% B-90%

Figure 11:
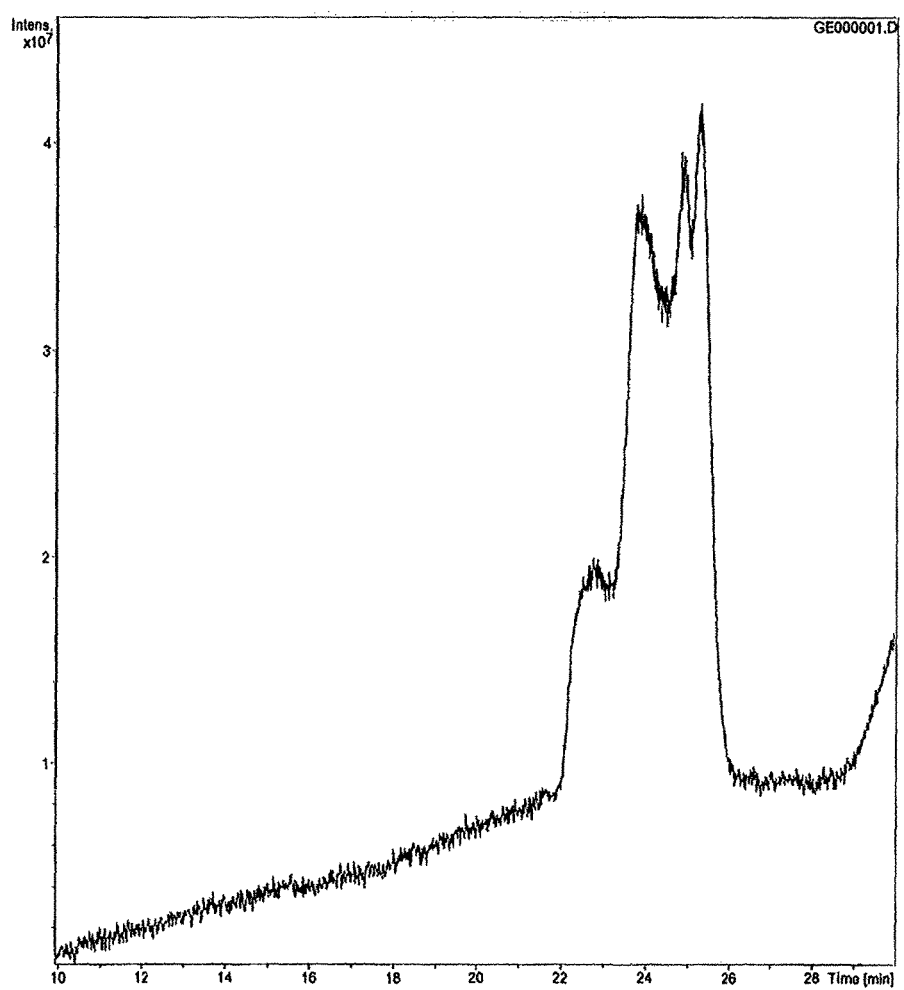
FIG. 11. Total ion count MS chromatogram from the sample obtained in Example 5 as a function of time.
Figure 12:
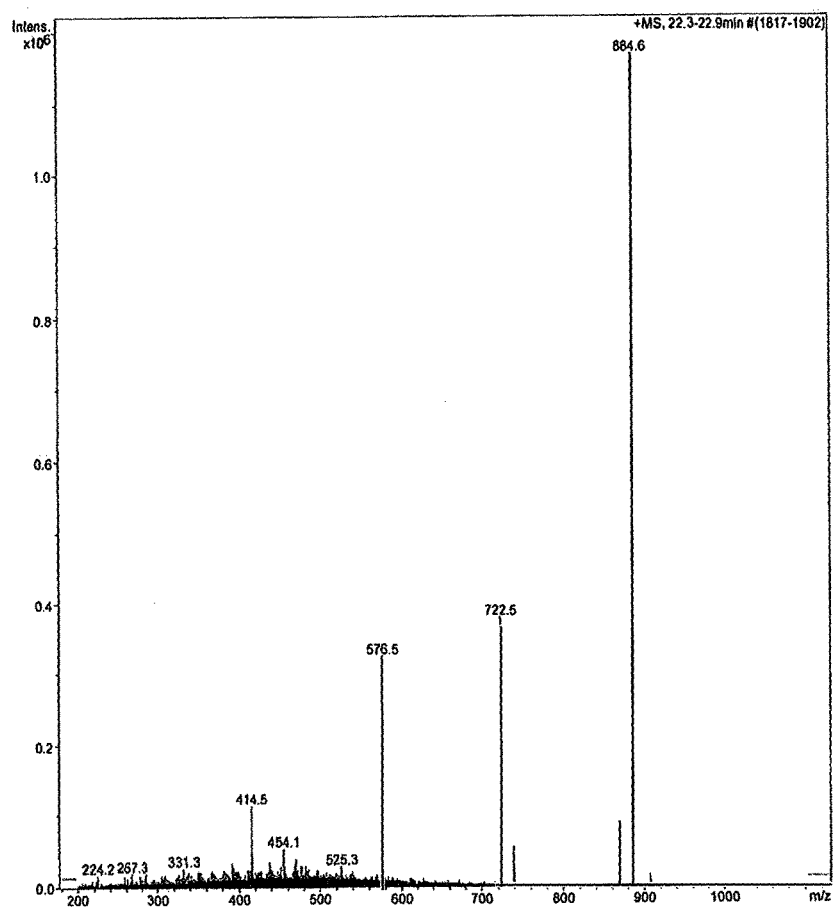
FIG. 12. The mass spectrum at 22.3-22.9 minutes from FIG. 11.
Figure 13:
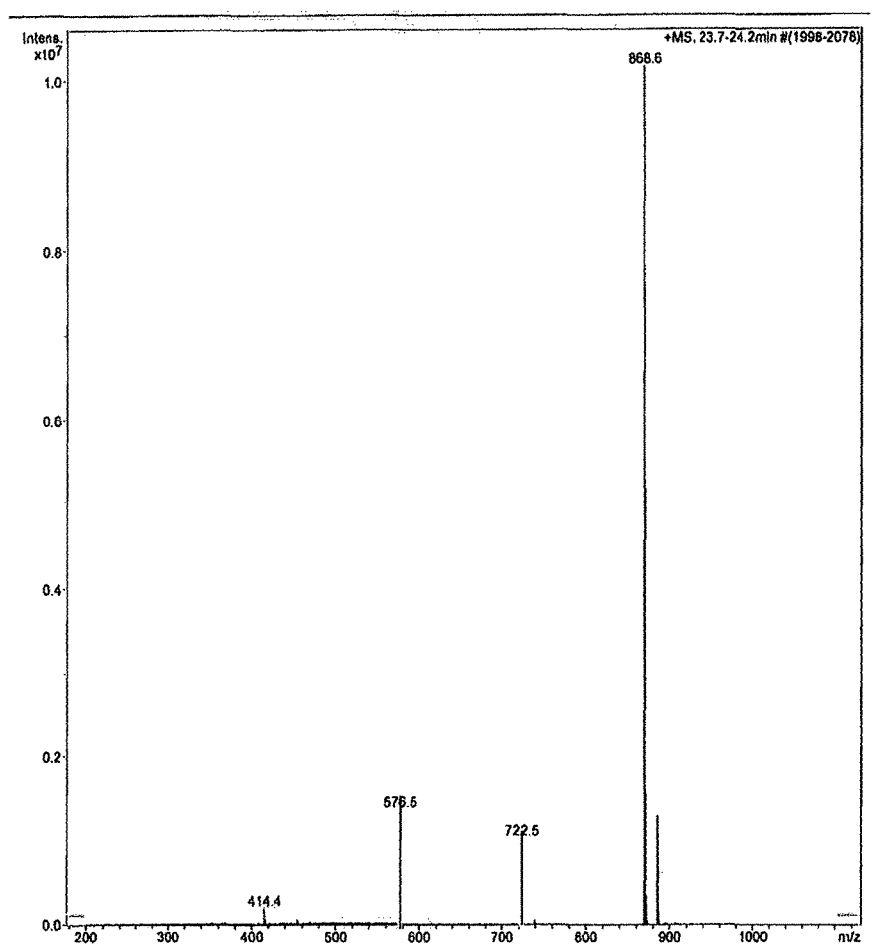
FIG. 13. The mass spectrum at 23.7-24.2 minutes from FIG. 11.
Figure 14:
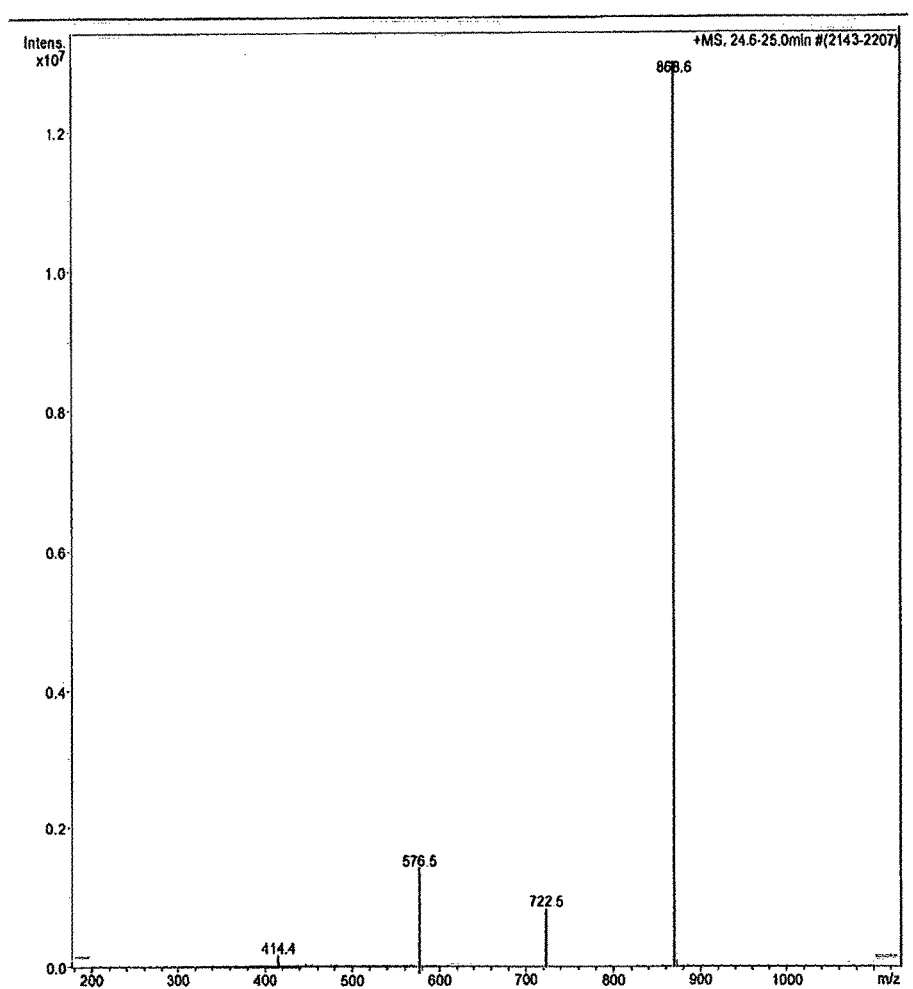
FIG. 14. The mass spectrum at 24.6-25.0 minutes from FIG. 11.
Figure 15:
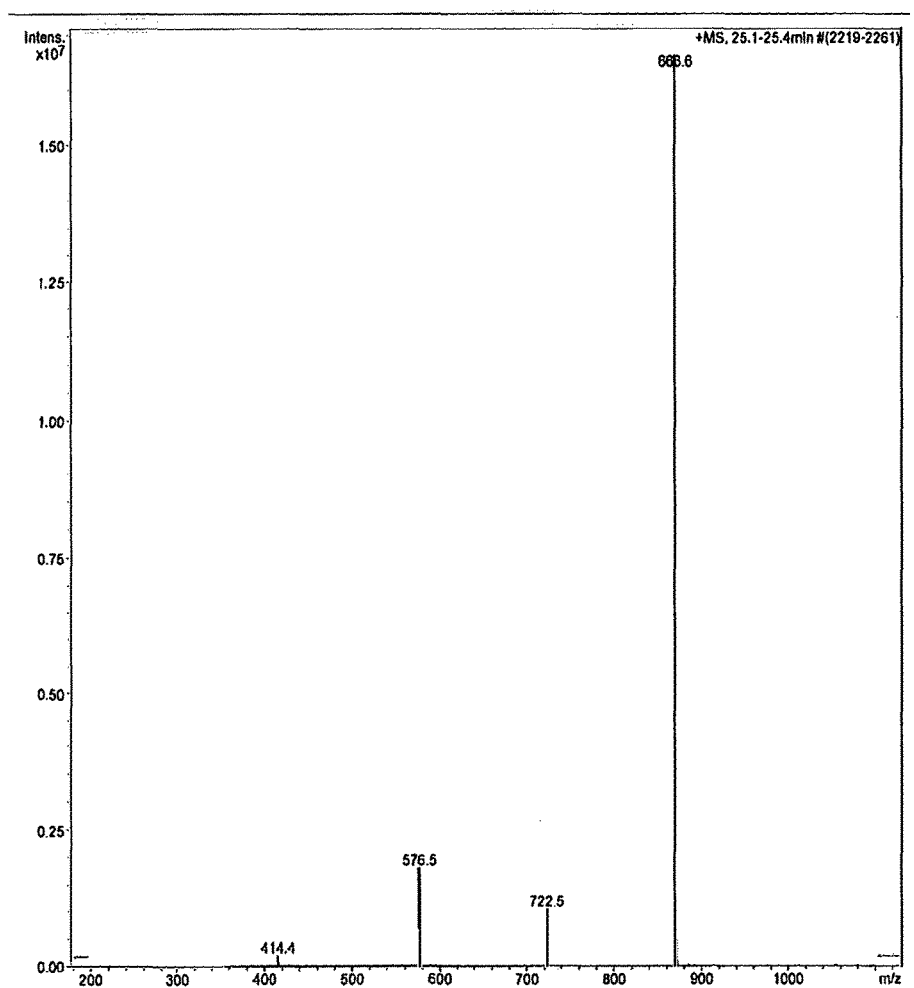
FIG. 15. The mass spectrum at 25.1-25.4 minutes from FIG. 11.
Figure 16:
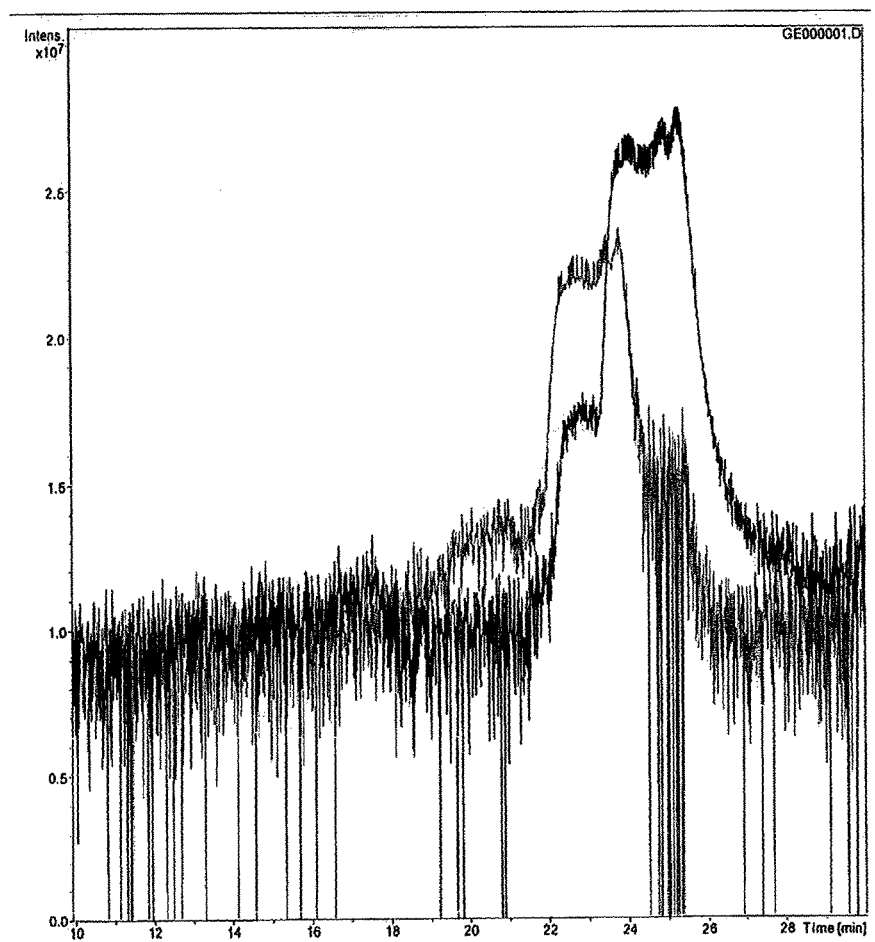
FIG. 16. Ion count for (M+H)+ ions at m/z 868 and m/z 884 from the sample obtained in Example 5 as a function of time.

FIG. 11 is the total ion count spectrum from the system with FIGS. 12-15 being mass spectral measurements taken at various different elution times as indicated on the spectra in the respective figures. The spectra showed two primary components having (M+H)+ ions at m/z 868 and m/z 884 indicative of components having a molecular weights of 867 and 883 respectively. By visual inspection of the mass spectral data it is apparent that the samples are of high purity. The individual ions, m/z 868 and 884, were both plotted as a function of retention in FIG. 16 with the y-axis representing ion counts. Using a trapezoidal measurement approach, an area count of 4.8×10$^7$ for m/z 868 and 2.21×10$^7$ for m/z 884 was estimated (the signal from 868 having a signal with a peak maximum at about 25.5 minutes and 884 having a signal with a peak maximum at about 24 minutes). Comparison of the area counts with the mass spectra and chromatographic data from Example 1 (and using the Example 1 data for reference) were used to estimate a purity of greater than 98%.

Example 7

Preparing Cosmetic and Therapeutic Compositions

Approximately 100 mg of each dry extract obtained using the present invention from *S. melongena, S. quitoense* y *S. lycopersicum* fruits, are mixed and crushed until obtaining a white, crystalline, with homogeneous consistence and even particle size powder.

The obtained powder is incorporated with suitable vehicles and excipients until getting a composition that can be liquid, semisolid or solid at a concentration between 0.0001% and 10.0%. The composition(s) can be used as depigmenting agents, sunscreens, anti-inflammatories, anti-bacterial and anti-fungal, to treat chronic skin conditions, such as non-melanoma skin cancer, leishmaniasis and other disorders caused by adverse environmental factors, like pollution and solar radiation.

Example 8

Preparing a Cosmetic Composition

To 12.01 Kg of water was added 0.6 Kg of salicylic acid with constant stirring for almost 30 minutes in a stainless steel vessel. Then, 1.44 Kg of triethanolamine was added slowly to complete dissolution and stirring for more than 1 hour. In a separate container, 3.0 Kg of urea in approx. 9.61 Kg of the water with constant stirring for 2 hours followed by subsequently dissolving 0.3 Kg of soluble Vitamin E.

In another separate container, to 2.4 Kg of water was added 1.8 Kg ethanol, and dissolve the 6.0 grams of saponins prepared generally in accordance with Example 1, and 6.0 grams of saponins extract obtained prepared generally in accordance with Example 5, with a constant and vigorous agitation for 20 minutes and gentle heating until a temperature of 40° C. was obtained to accelerate dissolution. Once the saponins extract was completely dissolved in the ethanol-water solution, the 3.0 Kg of Aloe Vera was mixed with a constant stirring for almost 15 minutes.

To the solution of urea add the saponin solution was added and mixed to homogenize with a continuous stirring for almost 30 minutes. 1.8 Kg of Salcare SC 91 was added slowly, with constant vigorous stirring until complete formation of the cream. This was then added to the triethanolamine and salicylic acid mixture until complete incorporation of it into the solution and it was further mixed for 20 minutes to homogenize. The final weight of the formulation was adjusted with water to obtain 24.0 Kg, mixed for 10 minutes to yield a white cosmetic skincare composition cream ready for packaging.

Example 9

Evaluation Test of Acute Dermal Toxicity

Acute Dermal Toxicity (TDA) was determined following the protocol indicated in the international guide OECD 402, in order to establish the possible adverse or harmful effects that could result, in Wistar rats, the topical application of a Solanum genus plant dry extract, obtained according to Example 1. For the testing, 13 healthy adult females and with intact skin were used, which were divided into three groups (Table 3).

The first group (Group A) was applied, in a shaved skin area of 10 cm², 20 mg of a semisolid formulation containing the extract obtained in Example 1 at a concentration of 0.01% w/v, while the second group (group B) underwent to 20 mg of the same semisolid formulation, but at a concentration of 0.05% w/v. The third group was not applied any formulation and was taken as control. The results are illustrated in Table 4:

TABLE 4

| Group | Number of animals | Animals with toxicity signs | Animals found dead | Animals killed during the test |
|---|---|---|---|---|
| A | 5 | 0 | 0 | 0 |
| B | 5 | 0 | 0 | 0 |
| Control | 3 | 0 | 0 | 0 |

None of the animals tested in the assay showed signs of pain or suffering, and there was not evidence of clinical signs or changes in normal behavior, confirming that the composition containing the extract rich in glycosides of Solasodine does not cause systemic toxicity or another adverse effect.

Example 10

Biological Activity Assay

The molluscicidal activity of a formulation for controlling Giant African Snail (*A. fulica*) was determined. The formula comprises several *Solanum* genus fruit extracts according to Example 1.

The assay was conducted in La Mesa, Támesis, Antioquia, Colombia, wherein it was collected *A. fulica* snails with a size between 4 and 7 cm of length. Nine of those recollected snails underwent to the product by aspersion, at a concentration of 50 ppm. Another nine snails were sprayed with deionized water and left under supervision. They were taken as control.

After a period of between 3 and 5 minutes, the immediate reactions of snails, including a slime overproduction and the destruction of the membranes were observed. After 12 hours, the snails sprayed with the product showed no signs of life, and snails sprayed with deionized water and used as control, did not show any adverse reaction.

Example 11

Survey

Seventeen females and five males were provided cosmetic skincare compositions of the invention. The skin care compositions comprised saponins prepared in accordance with the invention and contained solamargine and solasonine along with cosmetic excipients of the invention. The individuals took the between 0.5 mL and 1.0 mL of the product daily for between 30 and 60 days. All 22 individuals reported some improvement in skin condition after taking the cosmetic. The most improved area, 36.4% was skin texture followed by a combination of "texture, well-being, beauty, and health" at 13.6%. On a scale of 1 to 5 with 5 being the highest, 14 out of 22 reported a "5" whether the cosmetic improved skin appearance with 6 reporting a 4. 16 out of 22 gave the product a 5 for moisturizing (with the remaining 6 people voting a 4) and 13 out of 22 gave the product a 5 for skin health (with 7 people voting 4). All 22 said they would recommend the product to others.

The invention claimed is:

1. A process for preparing a mixture of saponins in a solid phase comprising
   a. treating plants from the *solanum* genus with a liquid comprising a first alcohol to form a first alcohol solution and plant material;
   b. treating the plant material with a first liquid comprising an acid to form an acid solution;
   c. treating the acid solution with the first alcohol solution to get a combined solution;
   d. treating the combined solution with a base to get a resulting solid;
   e. treating the resulting solid with a third liquid comprising a second alcohol to get a second alcohol solution;
   f. treating the second alcohol solution with a fourth liquid comprising a polarity modifying agent to form a mixture of saponins in a solid phase.

2. The process of claim 1 wherein the first alcohol solution comprises ethanol and water, the acid solution comprises acetic acid and water, the second alcohol solution comprises ethanol and water, and the fourth liquid comprises water and sodium chloride.

3. The process of claim 2 wherein no class 1 or class 2 solvent is used as an alcohol or a liquid during the process.

4. The process of claim 1 wherein the base is selected from the group consisting of sodium hydroxide, potassium hydroxide, lithium hydroxide, ammonium hydroxide, sodium carbonate, potassium carbonate and ammonium carbonate.

5. The process of claim 1 wherein the polarity modifying agent is an inorganic salt.

6. The process of claim 1 wherein the polarity modifying agent is selected from the group consisting of sodium chloride, potassium chloride, ammonium chloride, sodium sulfate, potassium sulfate, ammonium sulfate, sodium phosphate, potassium phosphate, ammonium phosphate, and mixtures thereof.

7. The process of claim 1 wherein the *Solanum* genus plants are selected from the group consisting of *Solanum agrarium, Solanum atropurpureum, Solanum betaceum, Solanum quitoense, Solanum marginatum, Solanum surattense Burm, Solanum crinitum, Solanum hirtum, Solanum lycocarpum, Solanum lycopersicum, Solanum macranthum, Solanum mammosum, Solanum melongena, Solanum nigrum, Solanum psychotrioides, Solanum sycophanta* and *S. xanthocarpum.*

8. The process of claim 1 wherein the solid phase comprises one or more of chaconine, solamargine, solasonine, solanidine, solanine, sycophantine and tomatine.

9. The process of claim 1 wherein the solid phase comprises solanine and solamargine.

10. The process of claim 1 wherein the combined solution comprises acetic acid and ethanol.

11. The process claim 1 wherein the resulting solid is treated with an acid solution followed by a base to purify the resulting solid.

* * * * *